US010395353B2

(12) United States Patent
Rong et al.

(10) Patent No.: US 10,395,353 B2
(45) Date of Patent: Aug. 27, 2019

(54) MODEL-BASED SCATTER IN MULTI-MODALITY MULTI-ENERGY SPECT RECONSTRUCTION

(71) Applicant: Siemens Medical Solutions USA, Inc., Malvern, PA (US)

(72) Inventors: Xing Rong, Schaumburg, IL (US); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/667,326

(22) Filed: Aug. 2, 2017

(65) Prior Publication Data

US 2018/0061031 A1 Mar. 1, 2018

Related U.S. Application Data

(60) Provisional application No. 62/382,148, filed on Aug. 31, 2016.

(51) Int. Cl.
*G06T 5/50* (2006.01)
*G06T 5/00* (2006.01)
*A61B 6/03* (2006.01)
*A61B 6/00* (2006.01)
*G06T 11/00* (2006.01)

(52) U.S. Cl.
CPC .............. *G06T 5/50* (2013.01); *A61B 6/037* (2013.01); *A61B 6/5205* (2013.01); *A61B 6/5235* (2013.01); *A61B 6/5258* (2013.01); *A61B 6/5282* (2013.01); *G06T 5/001* (2013.01); *G06T 11/003* (2013.01); *G06T 2207/10072* (2013.01); *G06T 2207/20224* (2013.01); *G06T 2207/30004* (2013.01)

(58) Field of Classification Search
CPC ........ G06T 5/50; G06T 5/001; G06T 11/003; G06T 2207/10072; G06T 2207/20224; G06T 2207/30004; A61B 6/037; A61B 6/5205; A61B 6/5235; A61B 6/5258; A61B 6/5282
USPC ................. 250/363.04, 363.03, 362, 363.02
See application file for complete search history.

(56) References Cited

U.S. PATENT DOCUMENTS

| | | | |
|---|---|---|---|
| 6,950,494 B2 | 9/2005 | Vija et al. | |
| 2003/0004405 A1* | 1/2003 | Townsend | A61B 6/032 600/407 |
| 2003/0156684 A1* | 8/2003 | Fessler | A61B 6/032 378/210 |
| 2008/0056550 A1* | 3/2008 | Kadir | G06T 11/006 382/131 |

(Continued)

*Primary Examiner* — David P Porta
*Assistant Examiner* — Blake C Riddick (57) ABSTRACT

In SPECT reconstruction, multi-modal reconstruction is combined with model-based multi-energy image formation. The scatter modeling of the model-based image formation uses resampling to facilitate convolution with the scatter kernels while maintaining resolution for the multi-energy projection. This combination of multi-modal and model-based multi-energy image formation simultaneously addresses the inaccuracy of the image formation process for complicated energy spectra and image blurring due to degradation of resolution. Varying the reconstruction by iteration may provide some of the benefits while reducing computational burden.

21 Claims, 2 Drawing Sheets

(56) References Cited

U.S. PATENT DOCUMENTS

| | | | |
|---|---|---|---|
| 2010/0014730 A1 | 1/2010 | Hahn et al. | |
| 2010/0030069 A1* | 2/2010 | Peter | G01T 1/1615 600/427 |
| 2012/0076385 A1* | 3/2012 | Kolthammer | G01T 1/1603 382/131 |
| 2013/0267841 A1 | 10/2013 | Vija | |
| 2013/0294570 A1* | 11/2013 | Hansis | G06T 11/005 378/4 |
| 2014/0003688 A1* | 1/2014 | Hansis | A61B 6/032 382/130 |
| 2014/0270443 A1* | 9/2014 | Vija | A61B 6/037 382/131 |
| 2015/0036789 A1* | 2/2015 | Panin | A61B 6/5235 378/4 |
| 2016/0116614 A1 | 4/2016 | Watson | |
| 2017/0086757 A1 | 3/2017 | Rong et al. | |
| 2017/0108596 A1 | 4/2017 | Ma et al. | |
| 2017/0164911 A1* | 6/2017 | Lv | A61B 6/037 |
| 2018/0061089 A1 | 3/2018 | Rong et al. | |

* cited by examiner

MODEL-BASED SCATTER IN MULTI-MODALITY MULTI-ENERGY SPECT RECONSTRUCTION

CROSS-REFERENCE TO RELATED APPLICATION

This application claims the benefit of priority under 35 U.S.C. § 119(e) of U.S. Provisional Patent Application Ser. No. 62/382,148, filed on Aug. 31, 2016, the disclosure of which is incorporated herein by reference.

BACKGROUND

The present embodiments relate to Single Photon Computed Tomography (SPECT). The reconstruction of a SPECT image is often difficult because the data is characterized by small signal rates and low signal-to-noise ratio. For SPECT imaging, the count rate is limited by the amount of a radionuclide (i.e., radioactive substance or radiotracer) that can be administered without harming the patient. Some radionuclides (e.g., Lu-177, I-123, Ga-67 and Y-90) have complicated energy spectra. For radionuclides with complicated spectra, the inaccurate model of the image formation process in iterative reconstruction may degrade the SPECT image. Multi-energy reconstruction may be used to benefit from the complicated energy spectra. Image blurring may still result due to degradation of resolution in the image formation process.

A SPECT image does not necessarily provide structural information. Thus, a SPECT image is often evaluated with the help of an adjacent structural image. Computed tomography (CT) may be used for the structural image. In multi-modality imaging, the CT data may be used as part of the SPECT reconstruction, such as by reconstructing separately for different types of tissue or zones. The zonal reconstruction may improve accuracy or resolution. When zonal reconstruction is used for radionuclides with complicated energy spectra (e.g., I-123 and Lu-177), due to the inaccurate image formation model, enhanced resolution does not necessarily lead to improved quantitative accuracy. In fact, resolution enhancement may reduce the quantitative accuracy. There are no SPECT reconstruction approaches that simultaneously address (a) the inaccuracy of the image formation process for complicated energy spectra and address (b) image blurring due to degradation of resolution.

SUMMARY

By way of introduction, the preferred embodiments described below include methods, systems, instructions, and computer readable storage media for SPECT reconstruction. Multi-modal reconstruction is combined with model-based multi-energy image formation. The scatter modeling of the model-based image formation uses resampling to facilitate convolution with the scatter kernels while maintaining resolution for the multi-energy projection. This combination of multi-modal and model-based multi-energy image formation simultaneously addresses the inaccuracy of the image formation process for complicated energy spectra and image blurring due to degradation of resolution. Varying the reconstruction by iteration may provide some of the benefits while reducing computational burden.

In a first aspect, a method is provided for SPECT reconstruction. CT data representing a region of a patient is obtained. Locations in the region are segmented between different types of anatomical tissue based on the CT data. The locations are zones segmented between the different types of the anatomical tissue. Separate zonal image objects are generated for each of the zones from measures of SPECT emissions of a radionuclide in the patient. The radionuclide having multiple energies, and the zonal image objects are at a first resolution. The measures of the SPECT emissions are reconstructed into a final image object. The reconstruction includes: separately forward projecting the zonal image objects for each zone into zonal data models of data space with multi-energy projectors, the multi-energy projector for each of the zones being for the multiple energies of the radionuclide; resampling the zonal image objects from the first resolution to a second resolution; modeling scatter with the resampled zonal image objects; correcting for scatter in the zonal data models with the modeled scatter for respective zones; and backward projecting residuals of a fit of a combination data model combined from the scatter corrected zonal data models. An image is generated as a function of the final image object.

In a second aspect, a method is provided for SPECT reconstruction. SPECT emissions are detected from a patient. The SPECT emissions are from a radionuclide with multiple energies. Anatomical information for the patient is acquired with an imaging modality different than SPECT. An image object is zonally reconstructed from the detected SPECT emissions and the anatomical information. The reconstruction uses model-based scatter correction for a multi-energy image formation model. An image is generated from the image object.

In a third aspect, multi-modal medical imaging system includes a computed tomography system configured to detect transmissions through a patient and a single photon emission computed tomography system configured to detect emissions from the patient. The emissions are from a radiotracer with distributed energies. A processor is configured to reconstruct an object representing the patient from the detected emissions for at least two energy windows of the distributed energies with a multi-energy image formation model and the detected transmissions. A display is configured to display an image of the reconstructed object.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multi-modality, multi-energy SPECT reconstruction is provided. The two important techniques used together improve both the quantitative accuracy and quality of SPECT images. Extending SPECT processes to include multi-energy tracers instead of a single energy tracer may not be straight forward. Extra-model information is combined with a multi-energy image formation model in an integrated framework. Different resampling of reconstructed images for different models in the multi-energy modeling allows both utilization of extra-model high resolution information and facilitates model-based scatter correction.

This combination simultaneously addresses two important problems. One is the inaccurate model of image formation process in iterative reconstruction, especially for radionuclides with complicated energy spectra (e.g., Lu-177, I-123, Ga-67, and Y-90). Another is the image blurring due to degradation of resolution in the image formation process. By combining zonal reconstruction and the model-based multi-energy image formation model, extra-modal information (e.g., CT, MRI, or another) improves SPECT image reconstruction and uses a more accurate image formation model to improve the quantitative accuracy of SPECT images. Both resolution and quantitative accuracy are improved. The combination is achieved by accounting for processes other than just performing both.

In one embodiment, the combination is used for Lu-177 dosimetry. Both the enhanced resolution and quantitative accuracy are crucial to accurate dosimetry. Zonal reconstruction provides more accurate segmentation of critical organs, and improved quantitative accuracy in the critical organs provides more accurate dosimetry. In another embodiment, simultaneous quantitative imaging of myocardial perfusion (Tc-99m) and innervation (I-123) is provided. Both accurate segmenation of the myocardium and accurate quantification are benefical to improving cardial SPECT imaging.

In reconstructing for multiple energy windows, separate projections for model-based scatter correction are provided for each of the different zones. This combination for iterative reconstruction is processing intensive. To reduce the processing, the forward projection for the model-based scatter correction may be handled for the total image rather than zones. The zone-based scatter correction may be used in earlier iterations and total image object-based scatter correction may be used in later iterations. This different strategy for zonal forward projection in different iterations achieves both high accuracy and fast reconstruction.

Figure 1:
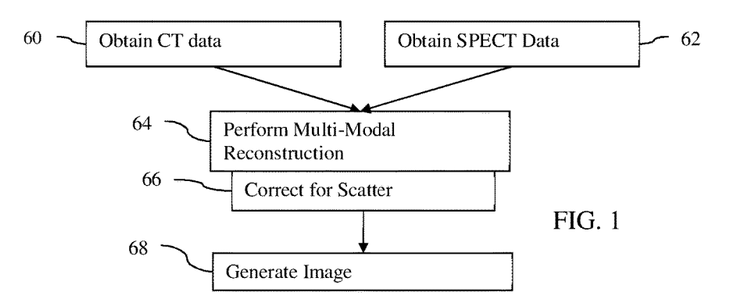
FIG. 1 is a flow chart diagram of one embodiment of a method for SPECT reconstruction.

FIG. 1 shows one embodiment of a method for SPECT reconstruction. By using a model-based multi-energy image formation in zonal reconstruction, resolution enhancement and improved quantitative accuracy may be simultaneously achieved.

Figure 4:
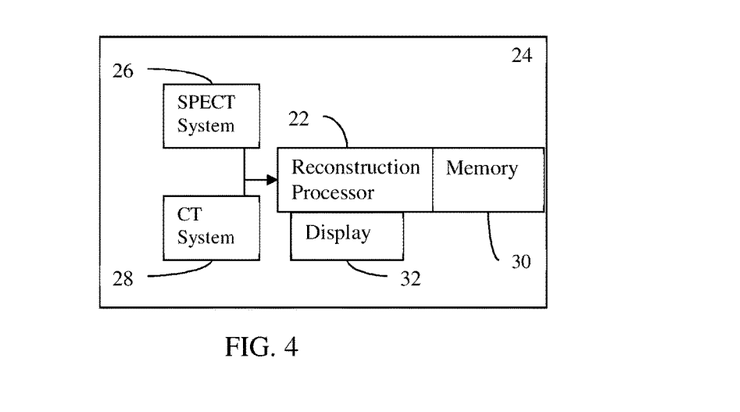
FIG. 4 is a block diagram of one embodiment of a system for SPECT reconstruction for radionuclides with complicated spectra.

The method of FIG. 1 is implemented using the system of FIG. 4, a processor, a computer, a CT scanner, a SPECT imager, and/or other device. For example, a CT scanner performs act 60, and a SPECT imager performs act 62. A computer performs acts 64-68, such as a computer of the SPECT imager or CT scanner.

The method is performed in the order shown (numerical or top to bottom), but other orders may be used. For example, acts 60 and 62 are performed simultaneously or in any sequence.

Additional, different, or fewer acts may be provided. For example, the CT data is used for attenuation correction. In another example, motion correction is performed. As another example, the generation of the image in act 68 is not performed.

In act 60, anatomical information for the patient is acquired with an imaging modality different than SPECT. Any imaging modality may be used, such as CT, magnetic resonance (MR), or ultrasound. The modality scans the patient to provide anatomical information about the patient in a same region from which emissions are to be detected by SPECT.

To provide higher resolution reconstruction, the measures of SPECT emissions are separated into zones for the reconstruction. In act 60, the anatomical information is obtained for creating the zones. The zones represent locations within the examined object and are derived from the anatomical information. The multimodal reconstruction may improve the image quality and/or reduce the acquisition time of the SPECT imaging process by considering the zonal information in the reconstruction.

In one embodiment, the support or anatomical information is obtained as CT data. The CT data is acquired by scanning the patient, by transfer, or from memory. A CT scanner scans the patient using a protocol (scan sequence), such as by transmitting x-rays and detecting the x-rays passing through the patient from different angles.

The CT data, reconstructed from the CT scanning, represents the same region of the patient as the SPECT data. The fields of view may be the same or different, such as overlapping. The CT data represents anatomical information about the examined object (e.g., shape, volume, thickness, and/or density of tissue types), type of disease and other disease specific features (e.g., density change within tissue (e.g. bone tissue), and/or calcification), type of application and other application specific features used to generate the image data (e.g., time dependence, and/or easily identifiable regions of lower interest but high signal (e.g. accumulation of a biomarker in the bladder)), and/or biomarker specific features (e.g., pharmacokinetic features, tissue types to which biomarkers attach, and/or time scale of processes for one, two, or more biomarkers).

The CT data and SPECT data are co-registered to provide registration. For example, anatomical CT data is co-registered with a preliminarily reconstructed image object.

The measurements for the CT data are Hounsfield (HU) measurements. For x-ray CT, the transmission spectrum is an attenuated Bremsstrahlung spectrum and thus continuous and depends upon the particular CT scanner and the attenuating body. The HU measurements are used to represent anatomy. Alternatively, the CT data is converted to linear attenuation coefficients. A p-map is generated from the CT information. This mu-map is used primarily for attenuation correction. But, because linear attenuation coefficients may more accurately represent different types of tissue than absorption measures despite differences in patient, protocol, and/or CT scanner, the mu-map serves well as a foundation for tissue segmentation. The conversion adapts the structural or support information to the CT scanner, the patient, and/or the protocol (see U.S. Pat. No. 6,950,494). Any conversion to a p-map may be used, but is adaptive for best results. Other methods of segmentation may be used, such as applying a deep-learnt classifier.

Linear attenuation coefficients are used in SPECT imaging for other purposes than defining zones. Attenuation correction is a prerequisite for quantitative SPECT imaging in nuclear medicine. CT data is used to derive linear attenuation coefficients suitable for compensating for attenuation along lines of response in the SPECT data. The same or different techniques for converting the CT data to linear attenuation coefficients may be used for zonal segmentation in multi-modal imaging.

In act 62, SPECT data is obtained. SPECT scanning is performed on a patient. In alternative embodiments, other functional imaging is performed, such as PET, fMRI or fCT. The SPECT data is measurements of SPECT emissions from a patient.

The SPECT data is obtained from scanning, from data transfer, or from memory. A SPECT system provides the SPECT data directly by scanning or indirectly by transfer or loading.

The activity concentration in a patient having received a radiotracer or radiotracers is determined as part of reconstruction by a SPECT system. After ingesting or injecting the radiotracer or tracers into the patient, the patient is positioned relative to a SPECT detector, and/or the SPECT detector is positioned relative to the patient. Emissions from the radiotracer or tracers within the patient are detected over time. A collimator in front of the detector limits the direction of photons detected by the SPECT detector, so each detected emission is associated with an energy and line or cone of possible locations from which the emission occurred. The lateral position of the line or cone relative to the detector may likewise be determined. The SPECT detector may be rotated or moved relative to the patient, allowing detection of emissions from different angles and/or locations in the patient.

The SPECT emissions are from a radionuclide with multiple energies. The emissions are at different energies. Energies at two or more levels or windows are detected. The energies are for chosen ranges whether from a continuous energy spectrum, from different major peaks, and/or from different minor peaks. For example, for I-123, there is a single main emission energy peak at 159 keV and a lot of low abundance emission high energy peaks. However, these higher emission energies penetrate the collimator and the effective abundance is higher, contributing to back ground due to scattering. Rather than use a single photon peak acquisition energy window around 159 keV, two models are used in reconstruction—one for emission energy peak 159 keV and another for all high-energy emission peaks. These two models have exactly the same acquisition energy window but different emission energies. In one embodiment, the emissions are generated by two or more radiotracers. Each radiotracer causes emissions at a different energy, such as using Tc-99m MIBI and I-123 MIBG for cardiac imaging. Any combination of two or more radiotracers may be used for a given scan of a patient (i.e., at a same time). In another embodiment, a radionuclide with different emission energies is used. For example, I-123, Lu-177 or In-111 is used. Lu-177 emits with energy peaks at 113 kv and 208 kv. Other peaks may not be included or may be included within the energy range set around one of the peaks being used. In yet another embodiment, Y-90 is used. The energy spectra of Y-90 is generally continuous rather than having specific peaks. The broad spectra may be approximated into quasi emission lines. Any two or more portions of the spectra may be used for multi-energy reconstruction.

Raw SPECT data or preprocessed data is provided for multi-modal reconstruction. The multimodal reconstruction may use a system matrix or projection operators to describe the properties of the SPECT imaging system to iteratively improve a data model of an image object representing the SPECT data. The image object may then be displayed using volume rendering or other imaging techniques.

The image object, which is defined in an object space, is a reconstruction of the SPECT data measured in a data space. The object space is the space in which the result of the image reconstruction is defined and which corresponds, for example, to the 3D volume (i.e., field-of-view or "FOV") that is scanned.

In act 64, a reconstruction processor zonally reconstructs an image object from the detected SPECT emissions and the anatomical information. Any zonal reconstruction may be used. For example, one of the zonal reconstructions disclosed in U.S. Published Patent Application Nos. 2010/0014730 or 2013/0267841 is used. The zonal reconstructions use multi-modal reconstruction to improve image quality. In multi-modal reconstruction, the anatomical information is segmented into zones. A zone is a 3D region of similar anatomical tissue. The segmentation is performed using an anatomical modality, such as CT. For example, bone tissue is segmented from non-bone tissue. Segmentation is provided by simple thresholding segmentation, gradient analysis, filtering, random walker, or other image processing based on the CT data. For CT, the segmentation is based on the measured units in CT, the Hounsfield (HU) scale, or based on linear coefficients of a $\mu$-map.

In the multi-modal reconstruction, a SPECT image of an examined object is reconstructed by considering the spatial or spatial-temporal structure of the object when approximating the SPECT image according to the acquired SPECT data. The structure of the object allows separating the object into multiple zones. Each organ or type of tissue is assigned to a separate zone. The volume within each of those zones is treated separately and equally in the reconstruction. Rather than equal treatment, the independence of the zones may be used for different treatment for different zones. Different amounts of signal are allocated to the zones according to the zone's contribution to the functional feature observed.

Multimodal reconstruction may impose a separation in anatomical zones of the reconstructed image object, but the zones do not modify the merit function of the applied reconstruction algorithm. The different zones are separately forward projected and renormalized as part of the iterative reconstruction. The result of multi-modal reconstructions may be increased resolution as compared to reconstruction with the functional information without multi-modal, even with attenuation correction.

The reconstruction includes use of multiple energy windows. For example, one of the multi-energy models in reconstruction disclosed in U.S. Published Patent Application No. 2017/0086757 is used. Since the various image degrading effects (e.g., scatter, attenuation, and/or collimator-detector response function) are different for different energy ranges, the forward projectors of the image formation process for photons at different energy ranges are modeled separately. In one embodiment, scatter, attenuation, and collimator-response functions are modeled separately for each of the different emission energies, emission energy ranges, and/or acquisition energy windows. One model handles the scatter, attenuation, and/or collimator-response function differently for different energies, providing separate models for separate energy windows.

Any type of scatter model may be used. Model-based scatter estimation is provided by modeling the physics of scatter in the patient. A Monte-Carlo simulation or other simulation may be used. Other physics or types of modeling of scatter may be used. The scatter may be modeled differently for different energies. Photons with different energies may scatter differently.

Any type of attenuation model may be used. For example, attenuation coefficients as a function of three-dimensional location in the patient are estimated from anatomical information provided by computed tomography (CT). The attenuation as emitted photons travel through tissue of the patient is modeled using the measured attenuation coefficients. Different energies attenuate differently, which may be modeled as different attenuation coefficients for different energies or a different scaling factor for the different energies.

Any type of collimator-detector response function model may be used. In one embodiment, point response functions are measured for the specific collimator and detector or for a class (i.e., type of collimator-detector pair). A Monte-Carlo or other simulation may be used. The point response function varies as a function of energy level. Other collimator-detector response functions may be used.

The image formation models for different energies are used for separate reconstructions at the different energies. The resulting image objects are then combined. Rather than totally separate reconstruction at each energy and post-reconstruction combination, the combination for the multiple photopeaks may be performed within or as part of reconstruction. Reconstruction is performed iteratively, so the combination for the multiple photopeaks is performed within the iteration loop of the reconstruction, such as combining back projected feedback of the different photopeaks for updating the volume. By combining feedback from the different photopeaks within the reconstruction, one image object is reconstructed for quantitative SPECT. Reconstruction using photon counts from multiple photopeaks in a combined way may increase the signal-to-noise ratio and improve image quality and quantitative accuracy for SPECT imaging.

For each photopeak, the image volume is projected and back projected with photopeak specific system matrix or projection operators (e.g., projection operators modeling attenuation correction, scatter correction, point response function, and/or sensitivity). The residuals, negradients (for conjugate-gradient method), or an analog resulting from back projection of the multiple photopeaks are combined. The image volume is updated by adding the conjugate gradient resulting from the combined negradients. For the update, the conjugate gradient is multiplied by an optimal step size based on the combined negradients. This reconstruction scheme combines multiple photopeaks in one image volume for quantitative SPECT. Alternatively, the combination is of image objects from different energies post-reconstruction.

The reconstruction includes forward projections for zone. For each zone, forward projections are performed for different energies using different image formation models. Part of the image formation models includes scatter correction in act 66. Any scatter correction may be used, such as energy window-based scatter correction. In one embodiment, model-based scatter correction is used. The scatter correction is performed as part of the forward projection from the image or object space to the data space. The scatter correction model is used in applying the image formation process to the activity distribution. The resulting projection data model has reduced scatter.

For model-based scatter correction, a scatter response function (SRF) is combined with the activity distribution of the patient to form a model-based scatter source. The SRF is represented by scatter kernels. The scatter kernels for the given SPECT system are used. The interaction of scatter resulting from different sources with a detector and collimator are simulated. Monte Carlo or other stochastic simulation may be used. The simulation is performed for all systems of a given type, such as all SPECT systems using a same combination of collimator and detector. The simulation is for that combination, such as based at least in part of the size, shape, and/or material characteristics of the collimator and detector. The simulation is not performed by the SPECT system, but by a computer, workstation, or server. Alternatively, the SPECT system performs the simulation. The results of the simulation are scatter kernels for the collimator and detector combination. The scatter kernels model the common physics in the image formation process for scatter.

The simulation is for a given radiotracer. The simulation provides for the source or sources to emit at the energy level for the primary photons. The simulation provides scatter kernels for different energy levels for the multi-energy image formation model.

The scatter kernels may be adapted to a specific SPECT system using measured sensitivity for that specific SPECT system. A measured sensitivity is used to normalize across the kernels, adapting the scatter kernels and resulting SRF to the specific collimator-detector combination. The sensitivity is measured at the energy level for the primary photons. Different sensitivities are provided for different energy levels or energy windows. The normalization is by the sensitivities for the primary photons or non-scattered energies from the radiotracer emissions at the different energies.

The scatter kernels are convolved with the activity distribution to create the model-based scatter source. The model-based scatter source is used to model detection of scatter by the SPECT system. The model-based scatter source generated from the scatter kernels is forward projected. This detection is modeled as the forward radiation transfer to create the model of scatter in the data space.

The forward projection of the activity distribution from the multi-energy image formation is combined with the model of scatter to reduce the scatter in the resulting projection data model for each zone. The image object or activity distribution for a given zone (i.e., zonal object) is convolved with the scatter kernels and also forward projected using the multi-energy formation model.

The image object for forward projecting is at a given resolution. The resolution may be a resolution of the CT or non-SPECT modality to increase SPECT resolution. In alternative embodiments, other resolutions are used. For modeling scatter, a different resolution is used. The image object for the zone is resampled, such as down-sampled or up-sampled. The scatter kernels are based on the energy resolution of the SPECT system, fitting the physics of the different energy windows. The resampling matches the image object resolution to the energy and spatial resolution of the SPECT system as represented by the scatter kernels. Different resampling of reconstructed images is provided for different models in multi-energy modeling.

The resampling matches the image object resolution to the SPECT system resolution rather than the resolution used for forward projection of the zonal image object. The zonal objects are used at one resolution for forward projecting the zonal objects and at one or more other resolutions for modeling scatter. Resampling is provided for each of the energies being used in the multi-energy reconstruction. In the image formation modeling process, to best incorporate high resolution information provided by the extra-model information, the voxel size of reconstructed images is set to be the same as the voxel size of input extra-model high resolution images. In the model of image formation process for primary photons, the voxel size of reconstructed images is not changed. In the model of scattered photons, however, to facilitate necessary convolution with scatter kernels, the reconstructed images (e.g., zonal image objects) are resampled so that the voxel size of resampled images is the same as the voxel size of scatter kernels.

In act 68, an image is generated from an image object output by the reconstruction. The reconstruction outputs an image object or volume representing the patient from a last iteration. This final image object is used for generating an image.

The image object is a three-dimensional representation of the detected emissions of the patient. The image object is rendered or otherwise used to generate an image. For example, a multi-planar reconstruction or single slice image of a plane is generated. The intersection of one or more planes with the image object is visualized. As another example, a surface or projection rendering is performed for three-dimensional imaging. Other imaging may be used.

One image is generated. Alternatively, a sequence of images is generated. For example, image objects from different time periods are used to generate a sequence of images representing the patient over time.

The image of the functional information from the multi-modal reconstruction is displayed alone. Alternatively, an anatomical image is displayed with the functional image. For example, the functional image is overlaid on a CT image. The overlay may be colored for display on a gray scale CT image. Other combinations may be used.

For quantitative SPECT, the image may be an alphanumeric text of a specific uptake value for a location. A graph, chart, or other representation of uptake at multiple locations may be output. The spatial image representing distribution of uptake may use color or brightness modulation to represent a level of uptake by location.

Figure 2:
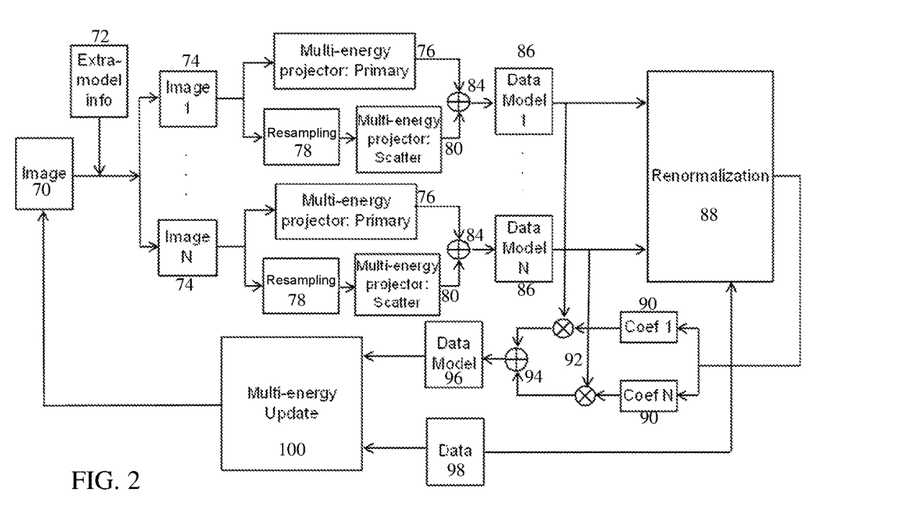
FIG. 2 is a flow chart diagram of one embodiment of a method for SPECT reconstruction with multi-modality, model-based, multi-energy reconstruction.

FIG. 2 is a flow chart diagram of one embodiment of a method for performing the multi-modal SPECT reconstruction of act 64. N zones are used for the zonal reconstruction. Two or more energies or energy windows may be used in the multi-energy image formation process. Using the zones based on extra modality (e.g., CT data 72), the multiple energy windows due to use of a radionuclide with a complex energy spectra, and model-based scattering, the measurements 98 of SPECT emissions are reconstructed into a final image object, the image object 70 of a last iteration.

The methods of FIG. 2 is implemented using the system of FIG. 4, a reconstruction, processor, a computer, a CT scanner, a SPECT imager (e.g., SPECT scanner), and/or another device. Additional, different, or fewer acts may be provided. For example, attenuation correction is performed.

An image object 70 is formed. The image object 70 is an initial reconstruction, default object, or an image object formed after any number of iterations of the reconstruction. The image object 70 is an estimate of a spatial distribution of emission locations from a patient. The counts or activity concentration at each location is included. The image object 70 is derived from the measures of SPECT emissions. The gamma camera detected emissions represent events along lines or cones of response. This data space representation is used to determine the image object 70, so the image object 70 is derived from the measures of SPECT emissions.

The emissions are from a radionuclide in the patient. The radionuclide is part of a radiotracer that binds, is activated, is absorbed, or is otherwise concentrated at locations of anatomical function. The radionuclide has a complex energy spectrum. Rather than having a single photopeak, the radionuclide emits at multiple separable photopeaks or over a range (e.g., continuous) of energies.

Zonal image objects 74 are formed from the image object 70. CT or other data 72 representing the patient is used to identify the zones. For example, different types of tissue are identified. Each type of tissue provides one of the zones. Any grouping of tissue may be used, such as soft tissue verses bone or different types of organs. In general, a zone includes object points with similar features. A zone need not be an enclosed area. The zone is continuous or discontinuous. The zones define spatial regions associated with a given grouping of one or more types of tissue. One zone may represent a target organ or target tissue of the biomarker used for the functional image. Any number of zones may be identified. Each zone is defined by locations in the volume at which that type of tissue occurs.

The CT or other data 72 is segmented to define the locations. Any segmentation may be used.

Separate zonal image objects 74 are generated for the zones. The measurements, such as the obtained SPECT data, are grouped by locations for the zones during reconstruction. Based on the zonal-information, zonal image objects 74 are prepared. Only the object points within the zone corresponding to the zonal image object 74 contribute to the reconstruction of the image object. During the reconstruction, the values of object points outside the zone do not contribute to the reconstruction of the zonal image object. Such values are constrained to be zero because one assumes that those object points do not generate any detected signal. The zonal image objects are generated for separate forward projection.

Multiplication of the image object 70 in object space with a zone-function restricts the entries of the object to be non-zero only at object points that are affiliated with the respective zone, creating the zonal image object 74. If, during the reconstruction, object points outside the zone are assigned with non-zero values, a repeated multiplication with the zone-function may be used to set those values to 0.

The generation of zonal information from the support information (e.g., linear attenuation coefficients) is performed by first identifying features of the examined object that relate to the functional measurement and then identifying the object points having the respective feature. In general, the areas defined by the zones abut each other. Smooth transitions may be enforced between zones.

The zonal objects 74 are at a same resolution as the image object 70 from which the zonal objects are created. Alternatively, the zonal objects 74 have a greater or lesser resolution than the image object 70. Since the anatomical information is available at a greater resolution than may typically be obtained by the SPECT system, the image object 70 and/or zonal objects 74 may be at a resolution of the anatomical data, such as at a resolution of the CT data 72. Other resolutions than the resolution of the CT or anatomical data 72 may be used.

Each zone includes the zonal image object 74, projectors 76, 80, resampling 78, and the zonal data model 86. These processes are performed separately for each zone.

Multi-energy projectors 76 forward project the zonal image objects 74. The forward projection simulates detection by the SPECT system of the zonal image object 74. Projection operators or a system matrix are used to determine a data model representing the projections of emissions detected by the SPECT system. Any forward projection may be used.

Multi-energy projectors 76 are applied to separately forward project the respective zonal image object 74. The result is a zonal data model 86 for each zone. The zonal data models 86 are in data space or emulate the measurements 98 of the SPECT emissions along lines of response defined by the collimator and position of the gamma camera.

The multi-energy projectors 76 forward project at different energy windows or ranges. The energy windows used are based on the radionuclide. Two or more distinct (with or without overlap) energy windows are defined to include photopeaks or higher energy regions of the energy spectra of the radionuclide. Any radionuclide with a complex spectra (e.g., multiple distinguishable peaks or region of substantially continuous (e.g., within 5 dB) energy) may be used, such as Lu-177, I-123, Ga-67, or Y-90.

Since the SPECT system may behave differently at different energies, the forward projectors of the multi-energy projectors 76 are different for different energies. The multi-energy projectors 76 use different models of attenuation and/or collimator-detector response function. Different modeling of scatter may be used and is separated out as the multi-energy projector 80 of scatter. For each zone, a zonal data model 86 is created for each energy.

The zonal image objects 74 are resampled 78 for modeling scatter with model-based scatter correction. Simulation is used to create scatter kernels representing the SPECT system response to scatter from many sources. By convolving the scatter kernels with the zonal image object 74, the sources of scatter for the SPECT system imaging this patient are modeled. Simulation is processing intensive, so is not performed for each patient. The simulation provides scatter kernels that can be more easily used to model sources of scatter for the patient.

The scatter kernels are at a resolution of the SPECT system or a different resolution than the CT data 72 and/or the zonal image objects 74. The difference in resolution is in energy and/or spatially. For modeling scatter, the zonal image objects 74 are resampled in energy and/or spatially. For example, the zonal image objects 74 are resampled from a resolution of the CT data 72 to another resolution, such as the lower resolution of the scatter kernels (e.g., SPECT system resolution without extra modality information (e.g., without CT data)). Any resampling may be used, such as down-sampling, decimation, up-sampling, interpolation, and/or extrapolation. Box car or other resampling approaches may be used. The resampling matches the zonal image object 74 to the energy windows and spatial resolution of the scatter kernels for the energy windows used for the radionuclide.

The resampled zonal image objects 74 are forward projected by multi-energy forward projectors 80. The multi-energy forward projectors 80 project simulated sources of scatter for the patient into a data model of scatter. The resampled zonal image objects 74 are convolved with the scatter kernels to create model-based scatter sources of scatter in the object domain. The forward projectors 80 model the scatter measured in the data domain or space by forward projecting the model-based scatter sources.

The model of scatter includes the multiple energy windows. The scatter at different energies of the radionuclide is modeled. Different projectors 80 are used for different energies.

The model of scatter in the data space is combined 84 with the projection of the zonal image object 74 by the multi-energy projectors 76. Zonal data models are combined with the modeled scatter. This combination removes scatter from the projection of the zonal image object 74. The model of scatter estimates which of the measures in data space are without scatter (i.e., from a primary emission) and which of the measures are from scatter. To correct for scatter, the measures in data space from scatter are removed. The measures in this case are the projections from the zonal image object 74, but are based in part on the actual measures 98 from the SPECT system as those actual measures 98 inform the creation and/or alteration of the image object 70.

This correction for scatter is performed for each zone. Since multi-energy projectors 76, 80 are used, the correction is performed for each energy as well. The zonal data model output by the multi-energy projectors 76 includes a data model for each energy window. Similarly, the model of scatter in data space output by the multi-energy projector 80 of scatter includes a scatter model for each energy window. The zonal data model for each energy is corrected by the scatter model for the corresponding energy in the combination 84. The result of the correction is the scatter corrected zonal data models 86. The scatter corrected zonal data models 86 are formed from the estimates of measures of the SPECT emissions without scatter.

For each zone, the same multi-energy projectors 76, 80 are used. Different projectors 76, 80 may be used for different zones. Each resulting zonal data model 86 includes data models for each energy window. Multiple zonal data models 86 corresponding to the different energies are provide for each zone.

The scatter corrected zonal data models 86 for each energy are to be combined 94. Due to the different operations in each zone, such as different zone functions, the total counts in the zonal data models 86 may vary between zones. Weights or coefficients 90 (i.e., zonal scaling factors) for each zone are determined by renormalization. The total counts in the zonal data models 86 are normalized to the total counts of the actual measurements 98. The determined coefficients 90 are multiplied 92 with the respective zonal data model 86. These normalized zonal data models 86 are then linearly combined 94 to create a full data model 96. Normalization may be performed at other parts of the reconstruction process, such as on the zonal image objects 74.

The full or combined data model 96 represents the estimated measures from the entire scan region represented by the full image object 70. Since multi-energy projectors 76, 80 are used, a combined data model 96 is provided for each energy window.

The multi-energy update 100 applies an objective function. The combined data model 96 is compared to the actual measures 98. This comparison indicates whether the image object 70 matches with the measurements 98 of the SPECT emissions. Any measure of fit may be used as the merit or objective function. For example, Poisson maximum-likelihood or Mighell's modified chi-square gamma fitting is used. A conjugate gradient method may be used.

The fit may be thresholded or another stop criterion applied. If the fit satisfies the stop criterion, then the image object 70 used for the most immediately previous forward projection is used as the reconstruction (i.e., final image object). Alternatively, any residuals are applied a last time to the image object 70, and the result is used as the final image object 70. If the fit does not satisfy the stop criterion, then the image object 70 is updated and another iteration of the reconstruction is performed.

The fitting produces feedback or residuals. The residuals represent differences between the complete data model 96 and the actual measures 98. Separate sets of residuals are provided for each energy window, resulting in a multi-energy update 100.

To update, the residuals are backward projected. Any backward projection may be used. The backward projection uses projection operators. A transpose of the system matrix or projection operators is applied to convert from the projection or data space to the image or object space. The transpose of the same projection operators 76 used for the forward projection are applied. Where at least one of the projection operators is energy dependent, the corresponding transpose is also energy dependent. Since the transpose of the backward projection are energy dependent, different transposed projection operators are used for the different photopeaks or energy ranges.

The backward projection converts the residuals in data space into the image space. The residuals in image space indicate changes to the image object 70. The feedback to be back projected is performed separately for the different energy ranges or photopeaks. For each of the multiple photopeaks, the reconstruction processor backward projects a difference of the measured emissions for the respective photopeak with the forward projection for the respective photopeak. The different sets of detected emissions are differenced from the different forward projections, respectively. For example, the forward projection at an energy range including 113 keV is subtracted from the measured emissions at the energy range including 113 keV, and the forward projection at an energy range including 208 keV is subtracted from the measured emissions at the energy range including 208 keV. The backward projection is performed separately for each of the multiple emission energies with corresponding transposes of the operators for the respective energy.

The information from the different energy windows is combined in the update of the image object 70. The combination may be of separately produced image objects. These image objects for the different energy windows are averaged or otherwise combined. The combination may be of the residuals from the different energies. Since a single volume is used, the feedbacks form the different emission energy ranges are combined for the volume. Any combination may be used, such as summation. The negradients from the back projections for the different photopeaks are summed. The combined negradients are used to correct the image or volume. The correction uses a conjugate gradient. The image object 70 is altered based on the residuals and, then, another iteration begins.

Zonal reconstruction with model-based multi-energy image formation uses many forward reprojection operations. This is processing intensive. The computational burden is proportional to the number of zones in forward projection and the number of energy windows. After a number, N, of iterations (e.g., 3-5), a different reconstruction may be used for the zonal reconstruction with model-based multi-energy image formation. FIG. 2 shows one embodiment of the reconstruction iteration operations for these first N iteration. To achieve high accuracy, in the first N iterations, all forward models in the multi-energy models are applied to separate zones.

Figure 3:
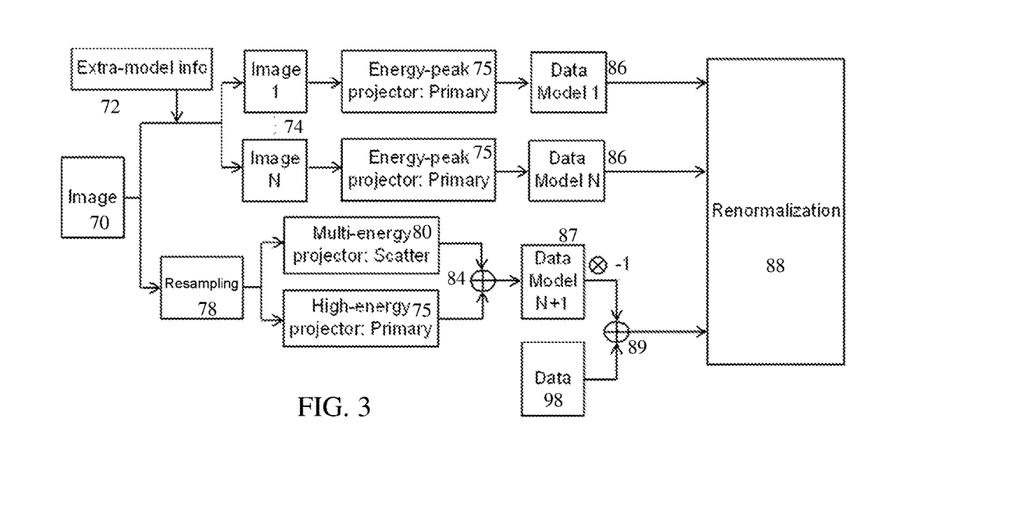
FIG. 3 is a flow chart diagram of one embodiment of a method for multi-modality, model-based, multi-energy reconstruction simplified for later iterations.

Since zonal effects are less important at later iterations and scatter and high energy penetrations have lower contrast in projection data, after N iterations, the forward models for scatter and high energy photons are applied to the whole image rather than separate zones. FIG. 3 shows one embodiment of the reconstruction iteration operations for the later iterations. Other or different simplifications may be used, such as handling scatter as a single energy window and/or no longer using zones. Reductions in processing may be provided by any combination of fewer energy windows being used, fewer zones being used, and/or using other scatter correction.

In FIG. 3, multi-energy projectors 80 are used for scatter modeling. The scatter modeled at different energies may not be used in the combination 84 where the image object is forward projected at just the high-energy. For the zonal forward projections, the energy-peak projector 75 forward projects for one or a single energy window. In FIG. 2, the model-based scatter correction is applied separately for different zones in a first number of iterations of the zonally reconstructing, and, in FIG. 3, the model-based scatter correction is used for a non-zoned image object 70 in a second number of iterations occurring after the first number of iterations. The complete image object 70 is resembled 78 for the modeling of scatter. For scatter correction, the model of scatter from the combined image object 70 is combined 84 with the data model forward projected at a highest energy window from the combined image object 70. Lower or other energy windows may be used, such as the same or different energy window used for the zonal image objects 74. The scatter corrected data model 87 is multiplied as a transpose and combined 89 with the measured data 98.

After the combination 89, the data models 86, 87 are normalized. The weighting, combination stop criterion application, and back-projection are not shown, but are performed as described for FIG. 2. This feedback may be for just one energy rather than multi-energy.

This variation in strategy for zonal forward projection in different iterations may achieve both high accuracy and fast reconstruction. This may speed up the reconstruction without sacrificing accuracy. In alternative embodiments, the less computationally intensive approach (e.g., FIG. 3) may be used for all iterations.

FIG. 4 shows one embodiment of a multi-modal medical imaging system. The system 24 implements multi-modal, model-based multi-energy reconstruction. The method of FIGS. 1, 2, and/or 3 or another method is implemented. Resampling is performed for zonal image objects and/or the complete image object to allow model-based scatter correction. Different reconstruction strategies or processes may be used for different iterations to provide the benefits of more computationally intensive approach and the reduction in time for reconstruction provided by less computationally intensive approaches.

The system 24 includes a reconstruction processor 22, a SPECT imaging system 26, CT imaging system 28, a memory 30, and a display 32. Additional, different, or fewer components may be provided. For example, a PET imaging system is provided instead of the SPECT imaging system 26. In one embodiment, the reconstruction processor 22, memory 30, and/or display 32 are part of one of the SPECT imaging system 26 or the CT imaging system 28. In alternative embodiments, the reconstruction processor 22, memory 30, and/or display 32 are provided as a workstation or computer separate from the imaging systems 26, 28. The memory 30 is part of a computer or workstation with the reconstruction processor 22 or is a remote database, such as a picture archiving and communications system (PACS).

The CT imaging system 28 is an x-ray source and detector mounted on a moveable gantry. The CT imaging system 28 is configured to detect transmission through a patient. The x-ray source generates x-rays, some of which pass through the patient. The detector detects the transmitted x-rays that pass through the patient. The energy used, timing, scan angles, and/or other aspects of the CT scan are set for a patient and used to scan a volume or other region of the patient. Any now known or later developed CT imaging system 28 may be used. While "imaging" is used herein, the CT imaging system 28 may be used to acquire data representing the patient without generating or displaying a CT image.

The SPECT imaging system 26 is any now known or later developed SPECT scanner. The SPECT imaging system 26 includes a detector for detecting emitted radiation from within the patient. For SPECT, a gamma camera is used to detect. The detector detects photon emissions. The photon is emitted from a tracer or radiopharmaceutical. The detector detects the photon. A given detector may detect a sequence of events from the same or different locations of the patient.

The tracer includes a radionuclide with a complex energy spectrum. Multiple energy peaks or a region of substantially continuous energy are provided. The radionuclide emits energies at or near the different energy peaks or within the continuous energy region.

The reconstruction processor 22 is a general processor, central processing unit, control processor, graphics processor, digital signal processor, application specific integrated circuit, field programmable gate array, amplifier, comparator, time-to-digital converter, analog-to-digital converter, digital circuit, analog circuit, timing circuit, combinations thereof, or other now known or later developed device for reconstructing a patient volume from detected emissions. The reconstruction processor 22 is a single device or multiple devices operating in serial, parallel, or separately. The reconstruction processor 22 is specifically designed or provided for reconstruction, but may be a main or general processor of a computer, such as a laptop or desktop computer, or may be a processor for handling tasks in a larger system. The reconstruction processor 22 may perform other functions than conversion, segmentation and reconstruction.

The reconstruction processor 22 is configurable. The reconstruction processor 22 is configured by software, firmware and/or hardware. Different software, firmware, and/or instructions are loaded or stored in memory 30 for configuring the reconstruction processor 22.

The reconstruction processor 22 is configured to reconstruct an object representing the patient from the detected emissions. The reconstruction is performed for at least two energy windows of the distributed energies of the radionuclide. A multi-energy image formation model and the detected transmissions are used. The reconstruction also includes zonal reconstruction. The CT data from the CT system 28 is used to segment or identify different zones.

The reconstruction processor 22 is configured to forward project a zonal image at a first resolution with multi-energy projectors and to model scatter with the zonal image at a second resolution different than the first resolution. The zonal images are resampled (i.e., sampled differently) for the primary multi-energy projection and the model of scatter. For example, the resolution of the zonal images is a resolution of the CT data, and the resolution for modeling scatter is a system or scatter kernel resolution.

The reconstruction processor 22 may be configured to alter the reconstruction. The reconstruction is iterative. A different reconstruction process may be used for later iterations than for earlier iterations. For example, the process of FIG. 2 is used for the first five iterations, and the process of FIG. 3 is used for any later iterations until the stop criterion is met.

The memory 30 is a random access memory, graphics processing memory, video random access memory, system memory, cache memory, hard drive, optical media, magnetic media, flash drive, buffer, database, combinations thereof, or other now known or later developed memory device for storing data. The memory 30 stores detected emissions (e.g., PET or SPECT detected event data), signals from transmission (e.g., CT data), zone information, segmentation information, energy information and/or reconstruction information. The memory 30 stores data as processed, such as storing an updated image object, zonal image objects, renormalization coefficients, scatter kernels, projection operators or system matrix, zonal data models, combined data models, zone functions, resampled image objects, and/or other information.

The memory 30 or other memory is a non-transitory computer readable storage medium storing data representing instructions executable by the programmed reconstruction processor 22 for SPECT reconstruction. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 32 is a monitor, LCD, plasma, touch screen, printer, or other device for displaying an image for viewing by a user. The display 32 shows one or more images representing function, such as uptake or activity concentration. The image is a quantitative or qualitative SPECT image. The image may be a volume rendering, a multi-planar reconstruction, a cross-section, and/or other image from a final image object. The image represents a distribution of the radionuclide in the patient based on detected emissions from the SPECT system 26.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for single photon emission computed tomography (SPECT) reconstruction, the method comprising:

obtaining computed tomography (CT) data representing a region of a patient;

segmenting locations in the region between different types of anatomical tissue based on the CT data, the locations comprising zones segmented between the different types of the anatomical tissue;

generating separate zonal image objects for each of the zones from measures of SPECT emissions of a radionuclide in the patient, the radionuclide having multiple energies, and the zonal image objects being at a first resolution;

reconstructing the measures of the SPECT emissions into a final image object, the reconstructing including:

separately forward projecting the zonal image objects for each zone into zonal data models of data space with multi-energy projectors, the multi-energy projector for each of the zones forward projects at least one of the zonal image objects using different models of attenuation, collimator-detector response function or a combination thereof for the multiple energies of the radionuclide, resampling the zonal image objects from the first resolution to a second resolution, modeling scatter with the resampled zonal image objects;

correcting for scatter in the zonal data models with the modeled scatter for respective zones, and backward projecting residuals of a fit of a combination data model combined from the scatter corrected zonal data models;

wherein the generating and the reconstructing are performed iteratively for iterative reconstruction, wherein a first iteration includes using the multi-energy projectors and wherein a second iteration uses a single energy window projector for forward projecting the zonal image objects, wherein the first iteration occurs before the second iteration; and generating an image as a function of the final image object.

2. The method of claim 1 wherein generating the separate zonal image objects comprises separately grouping an iterative image object derived from the measures of the SPECT emissions for locations into the respective zones.

3. The method of claim 1 wherein separately forward projecting comprises forward projecting with the multi-energy projector using multiple energy windows for Lu-177, I-123, Ga-67, or Y-90.

4. The method of claim 1 wherein separately forward projecting comprises forward projecting with the multi-energy projectors using different modeling of scatter for each of the energies.

5. The method of claim 1 wherein a contribution of each zone to the combination data model is weighted according to zonal scaling factors for the respective zones.

6. The method of claim 1 wherein the first resolution is a resolution of the CT data, and wherein resampling comprises resampling from the resolution of the CT data to a system resolution as the second resolution.

7. The method of claim 1 wherein resampling comprises down sampling.

8. The method of claim 1 wherein resampling comprises matching the zonal image objects to energy windows of the multiple energies.

9. The method of claim 1 wherein modeling the scatter comprises forming model-based scatter sources from convolution of the resampled zonal image objects with scatter kernels derived from a simulation of scatter and forward projecting the model-based scatter sources.

10. The method of claim 1 wherein correcting comprises combining the zonal data models with the modeled scatter.

11. The method of claim 1 wherein correcting comprises estimating which of the measures of the SPECT emissions of the zonal data models are without scatter and which of the measures of the SPECT emissions of the zonal data models are from scatter, and creating the scatter corrected zonal data models from the measures of the SPECT emissions without scatter.

12. The method of claim 1 further comprising renormalizing the zonal data models and combining the renormalized zonal data models into the combination data model.

13. The method of claim 1 further comprising fitting the combination data model with the measures of the SPECT emissions for each of the energies, and wherein backward projecting comprises combining the residuals for the energies.

14. The method of claim 1 wherein the second iteration includes the resampling and modeling of the scatter based on an image object with fewer zones than the first iteration.

15. The method of claim 1 wherein the second iteration includes the resampling and modeling of the scatter based on an image object without zones.

16. A method for single photon emission computed tomography (SPECT) reconstruction, the method comprising:

detecting SPECT emissions from a patient, the SPECT emissions being from a radionuclide with multiple energies;

acquiring anatomical information for the patient with an imaging modality different than SPECT;

iteratively and zonally reconstructing an image object from the detected SPECT emissions and the anatomical information, the reconstructing using model-based scatter correction for a multi-energy image formation model, wherein the model-based scatter correction uses scatter kernels adapted based on measured sensitivities for the multiple energies of the radionuclide, wherein a first iteration includes using the multi-energy image formation model, wherein a second iteration uses a single energy window projector for forward projecting zonal image objects, wherein the first iteration occurs before the second iteration; and generating an image from the image object.

17. The method of claim 16 wherein iteratively and zonally reconstructing using the model-based scatter correction comprises resampling the zonal image objects.

18. The method of claim 16 wherein iteratively and zonally reconstructing using the model-based scatter correction comprises using the zonal image objects at one resolution for forward projecting the zonal image objects and at another resolution for modeling scatter.

19. The method of claim 16 wherein iteratively and zonally reconstructing using the model-based scatter correction comprises using the model-based scatter correction separately for different zones in a first number of iterations of the zonally reconstructing and using the model-based scatter correction for a non-zoned image in a second number of iterations occurring after the first number of iterations.

20. A multi-modal medical imaging system comprising:

a computed tomography system configured to detect transmissions through a patient;

a single photon emission computed tomography system configured to detect emissions from the patient, the emissions from a radiotracer with distributed energies;

a processor configured to iteratively reconstruct an object representing the patient from the detected emissions for at least two energy windows of the distributed energies with model-based scatter correction for a multi-energy image formation model and the detected transmissions, wherein the model-based scatter correction uses scatter kernels adapted based on measured sensitivities for the at least two energy windows, wherein a first iteration includes using the multi-energy image formation model, wherein a second iteration uses a single energy window projector for forward projecting zonal image objects, wherein the first iteration occurs before the second iteration; and a display configured to display an image of the reconstructed object.

21. The multi-modal medical imaging system of claim 20 wherein the processor is configured to forward project a zonal image at a first resolution with multi-energy projectors and to model scatter with the zonal image at a second resolution different than the first resolution.

* * * * *